US00PP11380P

United States Patent [19]

Heims

[11] Patent Number: Plant 11,380

[45] Date of Patent: May 16, 2000

[54] HEUCHERA PLANT NAMED 'EBONY & IVORY'

[75] Inventor: Dan M. Heims, Portland, Oreg.

[73] Assignee: Terra Nova Nurseries, Inc., Tigard, Oreg.

[21] Appl. No.: 09/107,863

[22] Filed: Jun. 30, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Kent L. Bell
*Attorney, Agent, or Firm*—Klarquist Sparkman Campbell Leigh & Whinston, LLP

[57] ABSTRACT

A new and distinct hybrid of Heuchera plant characterized by dark ruffled foliage and white flowers in profuse panicles to 50 cm (20 in) in height.

1 Drawing Sheet

The present invention relates to a new and distinct hybrid of Heuchera that originated as a cross-pollination of Heuchera 'Whirlwind' (female parent, unpatented) and a ruffled, white flowered Heuchera seedling (male parent, unpatented) that remains unnamed.

The new Heuchera is a result of a controlled cross of the aforementioned plants at Terra Nova Nursery, Inc., in Canby, Oreg. This hybrid was selected from a large selection of seedlings. Seed and pollen parent plants were retained to observe habit and to compare with the instant plant. The new variety has been reproduced only by asexual propagation (division and tissue culture). Each of the progeny exhibits identical characteristics to the original patent and is unlike any Heuchera offered by any American nursery or book known to me as evidenced by the following characteristics:

(1) Fall and winter: Dark ruffled foliage.

(2) Spring and summer: White flowers.

Asexual propagation by division and tissue-culture as done in Tigard, Oreg., shows that the foregoing characteristics and distinctions come true to form and are established and transmitted through succeeding propagations.

BRIEF DESCRIPTION OF THE DRAWING

The drawing is a photograph of a two-year-old specimen of Heuchera 'Ebony & Ivory'. The drawing depicts the plant as true to type as is photographically possible.

DETAILED PLANT DESCRIPTION

The following is a detailed description of the new Heuchera hybrid based on observations of specimens in Canby, Oreg. The color descriptions are all based on The Royal Horticultural Society Colour Chart and the Amerian Rhododendron Society publication: "A CONTRIBUTION TOWARD STANDARDIZATION OF COLOR NAMES IN HORTICULTURE."

Foliage:

*Type.*—Evergreen.
*Shape.*—Ovate, 6-lobed.
*Length.*—9–10 cm (3.5–4 in).
*Width.*—7–8 cm (2.75–3.25 in).
*Petiole length.*—13–14 cm (5.25–5.5 in).
*Margins.*—Undulate-doubly serrate-dentate, ciliolate.
*Apex.*—Acute.
*Base.*—Cordate-imbricate.
*Texture.*—Slightly rugose.
*Leaf arrangement.*—Basal clump.
*Venation.*—Reticulate.

Size:

*Height.*—44 cm (3-year-old plant in Canby, Oreg.).
*Width.*—92 cm (3-year-old plant in Canby, Oreg.).

Flower:

*Petal count.*—5 petals.
*Petal shape.*—Oblong.
*Petal type.*—Fused.
*Flower type.*—Complete, calyx tube cylndrical, stamens not exserted.
*Flower shape.*—Campanulate.
*Flower size.*—To 1 cm.
*Ovary.*—Partly inferior.
*Carpels.*—2 cells.
*Stamens.*—5.
*Pollen.*—Limited production.
*Flower number.*—Average 80 per panicle.
*Peduncle width.*—3 mm tapering to 0.7 mm.
*Blooming habit.*—Hoary panicles to 50 cm (20 in).
*Bloom period.*—Late April to mid-June, with some re-bloom (in Oregon).
*Fragrance.*—Not fragrant.
*Lastingness.*—To 3 weeks (panicles on the plant). To 9 days (panicles off the plant).

Fruit:

*Type.*—Dehiscent capsule.
*Fertile.*—Of low fertility.

Disease: Plants grown in Canby, Oreg., show little susceptibility to diseases except for root rot when grown under wet conditions.

Hardiness: Cold tolerance is set at USDA Zone 4 (−34° to −29° C.). Upper heat tolerance is unknown.

Color Characteristics

Foliage:

*Mature leaves upper surface—spring.*—Close to R.H.S. Yellow Green Group 147A but darker; leaves may lighten to R.H.S. Yellow Green Group 147A with more sun exposure. Some leaves are R.H.S. Greyed Purple Group 187A.
*Upper surface, summer through winter.*—R.H.S. Yellow Green Group 147A.
*Lower surface.*—R.H.S. Greyed Purple Group 187B.

Flowers:

*Petal upper surface.*—R.H.S. Yellow White Group 159B.
*Petal lower surface.*—R.H.S. Yellow White Group 158C.

Peduncle: R.H.S. Yellow Green Group 148A suffused with R.H.S. Red Purple Group 59A.
Fruit: R.H.S. Green Group 143B.

DESCRIPTION OF PARENT PLANTS

Heuchera 'Whirlwind' is a Terra Nova Introduction from 1996. It has very ruffled, bronze foliage and small pink flowers. The unnamed parent plant has white flowers and was selected in 1995 for its ruffled, glossy green leaves and good white flowers. Both plants have their heritage in *Heuchera americana* and *Heuchera micrantha* crosses.

I claim:

1. A new and distinct hybrid of Heuchera plant substantially as shown and described, characterized by dark ruffled foliage and white flowers in profuse panicles to 50 cm (20 in) in height.

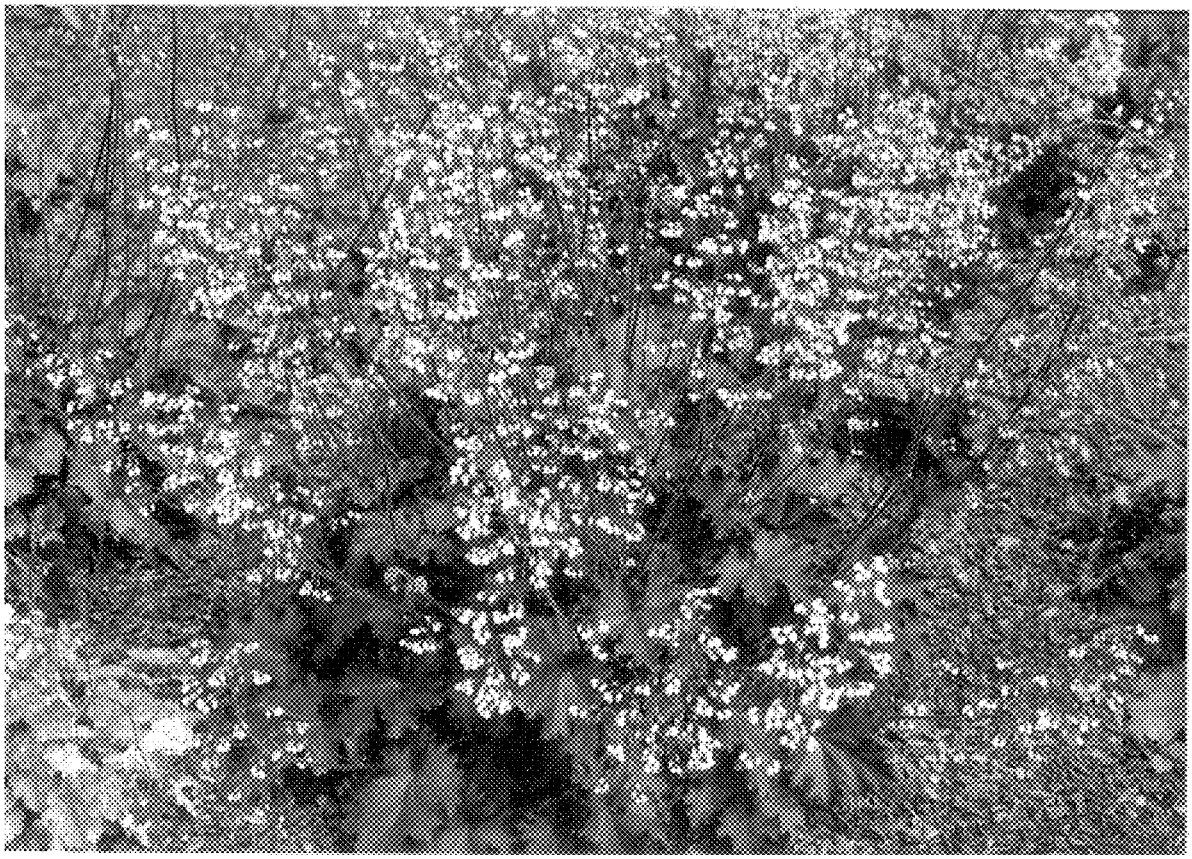

* * * * *